United States Patent [19]
Ramirez et al.

[11] Patent Number: 6,106,817
[45] Date of Patent: Aug. 22, 2000

[54] INSTANT LATHERING CLEAR SOLUTIONS AND GELS

[75] Inventors: Jose E. Ramirez, Trumbull; Mohan Vishnupad, Monroe, both of Conn.

[73] Assignee: Imaginative Research Associates, Inc., Milford, Conn.

[21] Appl. No.: 08/685,406

[22] Filed: Jul. 24, 1996

[51] Int. Cl.[7] .............................. A61K 7/075; A61K 7/48
[52] U.S. Cl. ......................................................... 424/70.19
[58] Field of Search ................................ 424/70.1, 70.19, 424/73

[56] References Cited

U.S. PATENT DOCUMENTS

| | | | |
|---|---|---|---|
| 2,995,521 | 8/1961 | Esrignard-Bluard . | |
| 4,726,944 | 2/1988 | Osipow et al. | 424/70 |
| 4,744,979 | 5/1988 | Osipow et al. | 424/73 |
| 4,772,427 | 9/1988 | Dawson et al. | 252/559 |
| 4,931,204 | 6/1990 | Ramirez et al. | 252/167 |
| 5,186,857 | 2/1993 | Ramirez et al. | 252/167 |
| 5,248,495 | 9/1993 | Patterson et al. | 424/73 |
| 5,254,334 | 10/1993 | Ramirez et al. | 424/70 |
| 5,429,815 | 7/1995 | Faryniarz et al. | 424/47 |

FOREIGN PATENT DOCUMENTS 0 453 238   10/1991   European Pat. Off. .

*Primary Examiner*—Donna C. Wortman
*Assistant Examiner*—Brenda G. Brumback
*Attorney, Agent, or Firm*—Dilworth & Barrese

[57] ABSTRACT

Novel clear solutions or gels containing a volatile hydrocarbon, surfactants and a coupling agent do not separate, but rather due to solubilization of the volatile hydrocarbon by the coupling agent, provide acceptable consumer products.

18 Claims, No Drawings

INSTANT LATHERING CLEAR SOLUTIONS AND GELS

BACKGROUND

1. Technical Field

The present disclosure relates to post-foaming detergent compositions. More specifically, the present disclosure relates to compositions containing unique combinations of surfactants and coupling agents that solubilize volatile hydrocarbons to provide instant foaming products such as, for example, instant foaming cleaners, shave creams or hair care products.

2. Background of Related Art

The importance and consumer applications of post-foaming detergent compositions are well established. For example, U.S. Pat. No. 4,726,944 discloses clear shampoo formulations which are aqueous solutions of water-soluble salts of lauryl sulfate, volatile hydrocarbon, a tertiary amine oxide and water soluble gums.

In U.S. Pat. No. 4,744,979 a clear formulation is provided by using aqueous soap solution and a surface active agent such as amine oxide or alkanolamides and a volatile water-soluble organic liquid.

U.S. Pat. No. 4,772,427 achieves a clear solubilized volatile hydrocarbon formulation by using water soluble anionic alkali metal $C_{10}$–$C_{16}$ alkyl ether sulfate, water dispersible ethoxylated fatty alcohol or fatty ester, isopropyl myristate, mono- or disaccharide and a blend of volatile hydrocarbons such as n-pentane and isobutane. However, U.S. Pat. No. 4,772,427 states at column 6, line 20–27 that "the omission of a single component adversely effects the unique properties of the total composition. Accordingly the criticality of the essential ingredients and the specificality of each ingredients is necessary in the formulation of the present novel post-foaming shower gel products."

In U.S. Pat. No. 5,186,857, an oil in water emulsion with foaming surfactants that are utilized to increase solubility of a volatile hydrocarbon.

It would be desireable to provide an instant foaming, clear solution or gel which has an application in cleansing hair or skin or any substrates such as fabric or hard surface which may require cleaning.

SUMMARY

It has now been discovered that it is possible to solubilize volatile hydrocarbons in a surfactant system containing a primary surfactant such as alkyl ether sulfate, amine oxide or combinations thereof using a unique solubilizer polyethylene glycol ether of propylene glycol oleate, generally identified as PEG 55 Propylene glycol oleate.

In another aspect, it has been found that polyoxyethylene sorbitol hexaoleate or PEG-80 sorbitan laurate can be used with some alkyl ether sulfates or amine oxide surfactants to solubilize volatile hydrocarbon solvents to achieve a clear solution or gel.

Another important finding of this disclosure is that the amphoteric surfactants by themselves do not solubilize volatile hydrocarbon solvents. However, in combination with alkyl ether sulfates or amine oxide and in the presence of PEG-55 propylene glycol oleate or polyoxyethylene sorbitol hexaoleate or PEG-80 sorbitan laurate clear solutions or gels can be formulated.

The resulting clear instant foaming liquid or gel will foam on a surface with or without the aid of water. The clear solution or gel will not self-foam when enclosed in a bottle and exposed to high temperatures such as 100–120° F. Accordingly, products made from the present compositions are consumer friendly and can withstand transportation and storage condition en route to the market place.

The instant foaming clear solution or gels described herein can be packaged in unpressurized containers such as bottles and pump bottles or pressurized barrier packages.

Appropriate mixtures of surfactants are chosen depending on the application of the products such as shampoos, mousse, hand wash, facial cleaners, shower gels, shaving cream or hard surface/fabric cleaners.

DETAILED DESCRIPTION OF PREFERRED EMBODIMENTS

Compositions and products in accordance with this disclosure contain a primary surfactant or combination of primary surfactants, optionally a secondary surfactant, water, a volatile hydrocarbon, and a coupling agent to solubilize the volatile hydrocarbon.

The surfactant or combination of surfactants should be soluble in water to produce a clear solution or gel.

Suitable primary surfactants include alkyl ether sulfates such as, for example, $C_{10}$–$C_{16}$ alkyl ether sulfates that contain between 2 and 10 moles of ethoxylation. Ammonium as well as metal alkyl ether sulfates are useful. A particularly useful surfactant in this class is sodium lauryl ether sulfate having two moles of ethoxylation.

Also useful as the primary surfactant are amine oxides, a non-ionic nitrogen containing surfactant. Particularly useful are tertiary amine oxides with one long hydrocarbon chain containing 12 to 14 carbon atoms. Within this class of non-ionic surfactants, lauryl dimethyl amine oxide is particularly useful. Lauryl dimethyl amine oxide is commercially available under the name Ammonyx LO from Stepan Co., Northfield, Ill.

Alkyl ether sulfates of the formula $(CH_2CH_2O)$—$ROSO_3M$ wherein M is a mononovalent cation and R is a $C_8$–$C_{18}$ hydrocarbon are also suitable for use as the primary surfactant. A particularly useful alkyl ether sulfate is sodium trideceth sulfate. Sodium trideceth sulfate is available under the name Standapol ES-13 from Henkel Corp., Special Chemical Division, Gulph Mills, Pa.

The amount of primary surfactant employed in the composition will depend on a number of factors including the end use of the composition, the desired foaming characteristics, and other ingredients present in the composition. A combination of primary surfactants can also be employed to formulate a desired product having particular characteristics. Normally, the primary surfactant or combination of surfactants will be present in an amount from about 3 to about 50 percent actives by weight of the final composition, preferably from about 5 to about 30 percent actives by weight of the final composition.

Optionally, one or more secondary surfactants can be included in the present compositions. For example, an amphoteric surfactant can be added as a foam booster. Suitable amphoteric surfactants include imidazolines, sultaines and betaines. One particularly useful amphoteric surfactant is coco-amidopropyl betaine such as Monateric CAB-LC which is commercially available from Mona Industry. When used, the secondary surfactant can be present in amounts up to about 25 percent by weight of the final composition on an actives basis. Preferably, the secondary surfactant is present in an amount from about 0.1 to about 20 percent actives by weight.

A volatile hydrocarbon is included in the present compositions to provide foaming upon use or as a propellant. The volatile hydrocarbon is used to enhance the foam produced by primary surfactant and is a gas producing agent, which when exposed to air and temperature will provide instant, copious lather. The volatile organic liquid foam enhancing agent preferably boils in the range of 25° C. to 50° C. at a atmospheric pressure. Such volatile organic liquids include saturated hydrocarbons such as n-pentane, iso-pentane, n-butane, isobutane; and $C_1$–$C_6$ alkyl ethers such as dimethyl either, diethyl ether, methylethyl ether and diisopropyl ether. The amount of volatile hydrocarbon in the compositions will depend upon the type of product being formulated and the function to be served by the volatile hydrocarbon. Normally, however, the volatile hydrocarbon will be present in an amount from about 1 to about 7 percent of the final composition, preferably from about 3 to about 4 weight percent.

The present compositions also contain an effective solubilizing amount of a coupling agent. An effective solubilizing amount is an amount sufficient to prevent any significant separation of the volatile hydrocarbon from the surfactant. Thus, for example, an effective amount will prevent the formation of a separate layer of the volatile hydrocarbon. Typically, an effective solubilizing amount will be from about 0.5 to about 7 percent by weight of the final composition, preferably about 2 to about 4 weight percent.

One coupling agent found to effectively solubilize volatile hydrocarbons is a polyethylene glycol ether of propylene glycol oleate PEG-55 propylene glycol oleate. In concentrations of 1–7% this coupling agent will solubilize volatile hydrocarbons such as n-pentane, iso-pentane, iso-butane and dimethyl ether in presence of the above-mentioned primary surfactants and water resulting in an clear solution or gel which is stable under normal or high temperature stored in regular bottles or pressurized aerosol bottles.

Other agents which solubilize certain volatile organic solvents in certain primary surfactants include polyoxyethylene sorbitol hexaoleate and PEG-80 sorbitan laurate. While less universal in their ability to solubilize volatile hydrocarbon solvents, these compounds are quite useful in certain applications such as those formulations exemplified hereinafter.

Water (preferably deionized) in an amount from about 10 to about 65 percent by weight of the final composition is also present in the novel compositions described herein.

In addition to the above-mentioned ingredients, the present instant foaming clear aqueous solution or gel may also contain a variety of non-essential ingredients. For example, water soluble gums, such as cellulosic polymers or natural gum, can be added impart desired aesthetic properties to the product. The clear gels and solutions may also contain humectant such as glycerin, sorbitol, propylene glycol etc. which provide moisturizing benefit to the skin or hair. Fragrance and color can be added to improve the cosmetic appearance of the product. Active ingredients such as triclosan, chlorhexidene gluconate or salicylic acid can also be dissolved in the surfactant system to provide an anti-bacterial functional product. Furthermore, small amounts of water soluble soaps such as palmitate or stearate of sodium/potassium or ammonium can be used to improve the foam stability for a shaving application. Similarly alkanolamide can be added to improve foam stability.

The clear solution or gel compositions achieved by means of PEG-55 propylene glycol oleate or polyoxyethylene sorbitol or PEG-80-sorbitan laurate can be packaged in any conventional non-pressurized glass or plastic bottles. In cases where isobutane or dimethyl ether is used as a post foaming solvent, a pressurized spray bottle or a pressurized barrier package must be used.

EXAMPLES

The following examples are presented to illustrate specific embodiments of the present compositions and methods. These examples should not be interpreted as limitations upon the scope of the invention. Comparative Examples are also presented to show the novel effects produced by the present compositions.

Comparative Examples A–E

Compositions are prepared containing primary surfactant (or a mixture of primary and secondary surfactants), volatile hydrocarbon and water, but no coupling agent. In preparing the compositions, the formulations of the compositions are reported in Table I.

All of the ingredients except n-pentane are mixed to produce a clear solution. Heat is used where needed to achieve a clear solution. This concentrate is then transferred to a narrow neck glass bottle and measured amount of n-pentane is added. A screw cap is used to secure the product in a bottle. The product is then gently shaken.

TABLE - I

|  | A | B | C | D | E |
|---|---|---|---|---|---|
| Sodium Lauryl Ether Sulfate (ES-2) (28% aqueous solution) | 50.00 | — | — | — | 30 |
| Lauryldimethylamine Oxide (30% solution) | — | 60 | — | 40 | — |
| Sodium Trideceth Ether Sulfate (30%) | — | — | 40 | — | — |
| Cocoamidopropyl Betaine | — | — | — | 20 | 10 |
| Water | 47 | 37 | 57 | 37 | 57 |
| n-pentane | 3 | 3 | 3 | 3 | 3 |

All the above compositions showed n-pentane separation at the top of the bottle within 24 hours. These comparative Examples clearly indicate that n-pentane is insoluble in a primary surfactant or a mixture of the primary surfactant and an amphoteric surfactant.

Examples 1–5

The formulations shown in Table II are prepared in the manner described in Comparative Examples A–E to show the effects of a coupling agent in the present surfactant compositions.

TABLE - II

|  | Ex. 1 | Ex. 2 | Ex. 3 | Ex. 4 | Ex. 5 |
|---|---|---|---|---|---|
| Sodium Lauryl Ether Sulfate (28% solution) | 50.00 | — | — | — | 30 |
| Lauryldimethylamine Oxide (30% solution) | — | 60 | — | 40 | — |
| Sodium Trideceth Sulfate (30%) | — | — | 40 | — | — |
| Cocoamidopropyl Betaine (30% solution) | — | — | — | 20 | 10 |
| PEG-55 Propylene Glycol Oleate | 3 | 3 | 3 | 3 | 3 |
| Water | 44 | 34 | 54 | 34 | 54 |
| n-pentane | 3 | 3 | 3 | 3 | 3 |

Each of the above compositions produces a clear liquid or a gel without any layer separation. When kept at room temperature or at higher temperatures such as 110° F.–120° F., these compositions will stay clear without any separation, indicating that complete solubilization of the volatile hydrocarbon in the primary surfactant has been achieved with the aid of the coupling agent.

Overnight standing at room temperature or in an oven at 100–120° F. will clear any air bubbles in the compositions that might form during mixing of the product. The end product is a clear solution where a coupling agent is used. This is quite a surprising result when compared to the distinct, separate layer of n-pentane that forms where no coupling agent is used such as in the formulation of Comparative Examples A–E shown in Table I.

Examples 6–9

To exemplify the use of other coupling agents, the formulations described in Table III are prepared.

TABLE - III

|  | Ex. 6 | Ex. 7 | Ex. 8 | Ex. 9 |
| --- | --- | --- | --- | --- |
| Sodium Trideceth sulfate (30%) | 40 | — | 40 | — |
| Lauryldimethylamine Oxide (30%) | — | 60 | — | 60 |
| Polyoxyethylene Sorbitol Hexaoleate | 3 | 3 | — | — |
| PEG-80 Sorbitan Laurate | — | — | 3 | 3 |
| Water | 54 | 54 | 54 | 54 |
| n-pentane | 3 | 3 | 3 | 3 |

All the above compositions prepared similarly as described above produce a clear solution with no separation of n-pentane.

Comparative Examples F–H and Examples 10–12

Compositions containing isobutane as the volatile hydrocarbon are prepared with and without a coupling agent to show the newly discovered effects of the coupling agent. The formulations are described in Table IV.

|  | F | G | H | Ex. 10 | Ex. 11 | Ex. 12 |
| --- | --- | --- | --- | --- | --- | --- |
| Sodium Alkyl Ether Sulfate (28%) | 50 | — | — | 50 | — | — |
| Sodium Trideceth Sulfate (30%) | — | — | 50 | — | — | 50 |
| Lauryldimethylamine Oxide (30%) | — | 60 | — | — | 60 | — |
| PEG-55 Propylene Glycol Oleate | — | — | — | 3 | 3 | 3 |
| Iso-butane | 4 | 4 | 4 | 4 | 4 | 4 |
| Water | 46 | 36 | 46 | 43 | 33 | 43 |

Composition F, G and H have two separate layers with a top layer of iso-butane indicating the insolubility of isobutane in the system. In Examples 10, 11 and 12 where a coupling agent is used, a clear solution or gel is provided indicating a total solubilization of the volatile hydrocarbon.

Comparative Examples I–L

The following formulations I–L containing isobutane are prepared:

|  | I | J | K | L |
| --- | --- | --- | --- | --- |
| Sodium Trideceth Sulfate (30%) | 40 | 40 | — | — |
| Lauryldimethylamine Oxide (30%) | — | — | 60 | 60 |
| Polyoxyethylene Sorbitol Hexaoleate | 3 | — | 3 | — |
| PEG-80 Sorbitan Laurate | — | 3 | — | 3 |
| Iso-butane | 4 | 4 | 4 | 4 |
| Water | 53 | 53 | 33 | 33 |

None of the above systems are clear, but rather are hazy and upon standing a white precipitate separates out. These formulations show that the particular coupling agent employed, which solubilize n-pentane or iso-pentane, are unsuitable in the above formulations for solubilizing isobutane Example 13

An antibacterial surgical scrub is prepared having the following composition:

Antibacterial Surgical Scrub

| Ingredient | wt % |
| --- | --- |
| Lauryldimethylamine Oxide (30%) | 40 |
| Cocoamidopropyl Hydroxysultaine (30%) | 20 |
| Chlorhexidine Gluconate (20% solution) | 20 |
| PEG-55 Propylene Glycol Oleate | 5 |
| Water | 12 |
| n-pentane | 3 |

The surgical scrub is a clear solution that provides good foaming upon use.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

We claim:

1. A composition comprising:
   a surfactant system including a primary surfactant selected from the group consisting of alkyl ether sulfates, amine oxides and combinations thereof and optionally a secondary surfactant selected from the group consisting of amphoteric surfactants, the secondary surfactant being present in an amount up to about 20 percent actives by weight of the final composition;
   a volatile hydrocarbon;
   water; and
   an effective volatile hydrocarbon-solubilizing amount of a polyethylene glycol ether of polypropylene glycol oleate.

2. The composition as in claim 1 wherein the surfactant system comprises an alkyl ether sulfate.

3. The composition as in claim 2 wherein the alkyl ether sulfate is a sodium lauryl ether sulfate or sodium trideceth sulfate.

4. The composition as in claim 1 wherein the volatile hydrocarbon is selected from the group consisting of saturated hydrocarbons, $C_1$–$C_6$ alkyl ethers and combination thereof.

5. The composition as in claim 1 wherein the volatile hydrocarbon is present in an amount from about 1 to about 7 percent by weight of composition.

6. The composition as in claim 1 wherein the surfactant system includes an amphoteric surfactant selected from the group consisting of imidazolines, betaines and sultaines.

7. The composition as in claim 1 further comprising an active ingredient.

8. The compositions as in claim 7 wherein the active ingredient is selected from the group consisting of triclosan, chlorohexidene gluconate and salicylic acid.

9. A composition comprising:
   from about 3 to about 50 weight percent on an actives basis of a primary surfactant selected from the group consisting of alkyl ether sulfates, amine oxides and combinations thereof;
   up to 20 weight percent on an actives basis of an amphoteric secondary surfactant selected from the group consisting of imidazolines, betaines, sultaines and combinations thereof;
   from about 1 to about 7 weight percent of a volatile hydrocarbon selected from the group consisting of n-pentane, iso-pentane, isobutane, dimethylether and mixtures thereof;
   from about 10 to about 65 weight percent water;
   from about 0.5 to about 7.0 weight percent of polyethylene glycol ether of propylene glycol oleate; and
   up to about 20 weight percent of one or more active ingredients.

10. A method for preventing separation of a volatile hydrocarbon from a surfactant system, the method comprising:
    forming an aqueous solution containing one or more surfactants selected from the group consisting of alkyl ether sulfates, amine oxides and combinations thereof and an effective volatile hydrocarbon-solubilizing amount of a polyethylene glycol ether of propylene glycol oleate;
    mixing a volatile hydrocarbon with the aqueous solution to form a clear solution or gel; and
    storing the clear solution or gel in a closed container.

11. A composition comprising:
    a surfactant system including a primary surfactant selected from the group consisting of sodium trideceth sulfate, amine oxides and combinations thereof and optionally a secondary surfactant selected from the group consisting of amphoteric surfactants, the secondary surfactant being present in an amount up to about 20 percent actives by weight of the final composition;
    pentane;
    water; and
    an effective pentane-solubilizing amount of Polyoxyethylene sorbitol hexaoleate or PEG-80 Sorbitan Laurate.

12. The composition as in claim 11 wherein the pentane is selected from the group consisting of n-pentane, iso-pentane, and combinations thereof.

13. The composition as in claim 11 wherein the pentane is present in an amount from about 1 to about 7 percent by weight of the composition.

14. The composition as in claim 11 wherein the surfactant system includes an amphoteric surfactant selected from the group consisting of imidazolines, betaines and sultaines.

15. The composition as in claim 11 further comprising an active ingredient.

16. The composition as in claim 15 wherein the active ingredient is selected from the group consisting of triclosan, chlorohexidene gluconate and salicylic acid.

17. A composition comprising:
    from about 3 to about 50 weight percent on an actives basis of a primary surfactant selected from the group consisting of sodium trideceth sulfate, amine oxides and combinations thereof;
    up to 20 weight percent on an actives basis of an amphoteric secondary surfactant selected from the group consisting of imidazolines, betaines, sultaines and combinations thereof;
    from about 1 to about 7 weight percent pentane;
    from about 10 to about 65 weight percent water;
    from about 0.5 to about 7.0 weight percent of polyoxyethylene sorbitol hexaoleate or PEG-80 sorbitan laurate; and
    up to about 20 weight percent of one or more active ingredients.

18. A method of preventing separation of pentane from a surfactant system, the method comprising:
    forming an aqueous solution containing one or more surfactants selected from the group consisting of sodium trideceth sulfates, amine oxides and combination thereof and an effective pentane-solubilizing amount of polyoxyethylene sorbitol hexaoleate or PEG-80 sorbitan laurate;
    mixing pentane with the aqueous solution to form a clear solution or gel; and
    storing the clear solution or gel in a closed container.

* * * * *